(12) United States Patent
Ekeland

(10) Patent No.: US 8,722,153 B2
(45) Date of Patent: May 13, 2014

(54) RELEASE COATING COMPOSITION AND METHOD OF FORMING THE SAME

(75) Inventor: Robert Ekeland, Midland, MI (US)

(73) Assignee: Dow Corning Corporation, Midland, MI (US)

( * ) Notice: Subject to any disclaimer, the term of this patent is extended or adjusted under 35 U.S.C. 154(b) by 957 days.

(21) Appl. No.: 12/601,875

(22) PCT Filed: May 23, 2008

(86) PCT No.: PCT/US2008/006647
§ 371 (c)(1),
(2), (4) Date: Nov. 25, 2009

(87) PCT Pub. No.: WO2008/153767
PCT Pub. Date: Dec. 18, 2008

(65) Prior Publication Data
US 2010/0166970 A1    Jul. 1, 2010

Related U.S. Application Data

(60) Provisional application No. 60/940,177, filed on May 25, 2007.

(51) Int. Cl.
*C09D 183/04* (2006.01)
*C23C 28/00* (2006.01)

(52) U.S. Cl.
USPC ........ 427/427.4; 428/447; 524/588; 524/862; 528/15; 528/39

(58) Field of Classification Search
USPC ............... 427/427.4; 428/447; 524/588, 862; 528/12, 15, 32, 39
See application file for complete search history.

(56) References Cited

U.S. PATENT DOCUMENTS

| | | | |
|---|---|---|---|
| 4,609,574 A | 9/1986 | Keryk et al. | |
| 6,147,243 A | 11/2000 | Onodera et al. | |
| 6,489,407 B1 * | 12/2002 | Clark et al. | 525/478 |
| 6,586,535 B1 | 7/2003 | Clark et al. | |
| 6,805,914 B2 | 10/2004 | Clark et al. | |
| 6,806,339 B2 | 10/2004 | Cray et al. | |
| 7,135,512 B2 | 11/2006 | Kilgour et al. | |
| 7,560,167 B2 | 7/2009 | Schlitzer et al. | |
| 7,592,412 B2 | 9/2009 | Cray et al. | |
| 2002/0061998 A1 | 5/2002 | Cray et al. | |
| 2005/0059776 A1 | 3/2005 | Cray et al. | |
| 2007/0289495 A1 | 12/2007 | Cray et al. | |
| 2008/0281055 A1 * | 11/2008 | Schlitzer et al. | 525/478 |

FOREIGN PATENT DOCUMENTS

| | | | |
|---|---|---|---|
| EP | 1002823 A1 | 5/2000 | |
| EP | 1070734 A2 * | 1/2001 | |
| JP | 2001-064390 A | 3/2001 | |
| JP | 2004-501264 A | 1/2004 | |
| JP | 2006-506510 A | 2/2006 | |
| JP | 2008-520804 A | 6/2008 | |
| JP | 2009-513740 A | 4/2009 | |
| JP | 2010-502778 A | 1/2010 | |
| WO | WO 03/093369 A1 | 11/2003 | |
| WO | WO 2005/005544 A1 | 1/2005 | |
| WO | WO 2005005544 A1 * | 1/2005 | |
| WO | WO 2006/055233 A1 | 5/2006 | |

OTHER PUBLICATIONS

PCT International Search Report for PCT/US2008/006647, dated Feb. 20, 2009, 4 pages.
English language abstract and machine-assisted English translation for JP 2001-064390 extracted from the PAJ database on Jan. 27, 2014, 49 pages.
English language abstract not available for JP 2004-501264; however, see English language equivalent US 6,586,535. Original document extracted from the espacenet.com database on Jan. 27, 2014, 50 pages.
English language abstract not available for JP 2006-506510; however, see English language equivalent US 7,135,512. Original document extracted from the espacenet.com database on Jan. 27, 2014, 16 pages.
English language abstract not available for JP 2008-520804; however see English language equivalent US 2007/0289495. Original document extracted from the espacenet.com database on Jan. 27, 2014, 30 pages.
English language abstract not available for JP 2009-513740; however, see English language equivalent US 7,592,412. Original document extracted from the espacenet.com database on Jan. 27, 2014, 20 pages.
English language abstract not available for JP 2010-502778; however, see English language equivalent US 7,560,167. Original document extracted from the espacenet.com database on Jan. 27, 2014, 13 pages.

* cited by examiner

*Primary Examiner* — Alexander Weddle
(74) *Attorney, Agent, or Firm* — Howard & Howard Attorneys PLLC

(57) ABSTRACT

A release coating composition includes a curable polysiloxane and an aerosol suppressant that has more than one $SiO_{4/2}$ unit. The aerosol suppressant includes the polymerization product of a siloxane and a cyclic polysiloxane polymerized in the presence of a polymerization catalyst. The siloxane has units of the chemical formula $(SiO_{4/2})(R^aR^b{}_2SiO_{1/2})_x$ wherein Ra is a vinyl moiety, $R^b$ is an alkyl moiety, and x is a number from 1.05 to 4. The release coating composition is formed by combining the aerosol suppressant and a curable polysiloxane. The release coating composition is also used to coat a substrate in a release coating process producing a mist of less than 50 mg/cubic meter measured at approximately 457 m/min.

29 Claims, No Drawings

RELEASE COATING COMPOSITION AND METHOD OF FORMING THE SAME

RELATED APPLICATIONS

This application claims priority to and all the advantages of International Patent Application No. PCT/US2008/006647, filed on May 23, 2008, which claims priority to U.S. Provisional Patent Application No. 60/940,177, filed on May 25, 2007.

FIELD OF THE INVENTION

The present invention relates to a release coating composition and a method of forming the same. The release coating composition comprises an aerosol suppressant and a curable polysiloxane. The present invention also relates to a method of coating a substrate with the release coating composition.

DESCRIPTION OF THE RELATED ART

Release coating compositions that include silicone are well known in the art and are used in a wide variety of applications such as on single and double sided liners. Examples of single sided liners include backing papers for pressure sensitive adhesive labels which typically require temporary retention without reduction in adhesion. Examples of double sided liners include interleaving papers for transfer tapes and adhesive films. These double sided liners provide protection for, and ensure desired unwind characteristics of, the tapes and films.

The release coating compositions can be applied to substrates, such as the single and double sided liners, in high speed release coating processes at speeds of about 305 meters/min and faster. When applied to these substrates, the release coating compositions tend to form "mists" which include particles of the composition finely dispersed in the air. These mists are not only wasteful but are also production nuisances which coat machinery and floors of production facilities.

The release coating compositions can be formed through a variety of synthetic processes. These processes are typically low yield, cost prohibitive, and unable to produce release coating compositions that have a decreased tendency to mist when used in the high speed release coating processes.

Accordingly, there remains an opportunity to provide a release coating composition that can be applied to substrates in high speed release coating processes with minimized mist. There also remains an opportunity to develop a method of forming the release coating composition and a method of applying the release coating composition to substrates.

SUMMARY OF THE INVENTION AND ADVANTAGES

The present invention provides a release coating composition comprising an aerosol suppressant and a curable polysiloxane wherein the aerosol suppressant has more than one $SiO_{4/2}$ unit produced by the polymerization product of a siloxane and a cyclic polysiloxane in the presence of a polymerization catalyst.

The present invention also provides a method of forming the release coating composition wherein the method comprises combining the aerosol suppressant and the curable polysiloxane to form the release coating composition. The present invention further provides a method of coating a substrate in a release coating process wherein the coating method comprises applying the release coating composition to a substrate.

The release coating composition of the present invention is formed in a cost-effective manner and applied to a variety of substrates with reduced mist. When used in high speed release coating processes, the aerosol suppressant minimizes atomization of the release coating composition, thereby reducing waste and nuisance. Specifically, it is believed that the more than one $SiO_{4/2}$ unit of the aerosol suppressant contributes to this mist reducing effect. Additionally, the aerosol suppressant is effectively formed through polymerization of the siloxane and the cyclic polysiloxane in the presence of the polymerization catalyst. This catalyst efficiently directs incorporation of the $SiO_{4/2}$ units in a broad siloxane matrix thereby producing the aerosol suppressant.

DETAILED DESCRIPTION OF THE INVENTION

The instant invention provides a release coating composition, hereafter simply referred to as "composition." The composition includes an aerosol suppressant and a curable polysiloxane. Without intending to be bound by any particular theory, it is believed that the aerosol suppressant decreases the tendency of the composition to mist, i.e., to atomize and form finely dispersed particles in the air. The tendency of the composition to mist is measured when the composition is applied to a substrate.

The aerosol suppressant has more than one $SiO_{4/2}$ unit (Q unit) and may have any whole number or fraction of $SiO_{4/2}$ units greater than one. In one embodiment, the aerosol suppressant has from 1.05 to 4 $SiO_{4/2}$ units. Alternatively, the aerosol suppressant may have at least two $SiO_{4/2}$ units or may have from two to four $SiO_{4/2}$ units. For descriptive purposes only, a chemical structure of a $SiO_{4/2}$ unit is shown below:

$$\begin{array}{c} | \\ O \\ | \\ -O-Si-O- \\ | \\ O \\ | \end{array}$$

The aerosol suppressant may also include $R^b{}_2SiO_{2/2}$ units (D units). $R^b$ may be independently selected from the group of an alkyl moiety having from 1 to 6 carbon atoms, an aryl moiety, an alkoxy moiety, an acrylate moiety, and a methacrylate moiety. The alkyl moiety may include, but is not limited to, methyl moieties, ethyl moieties, propyl moieties, iso-propyl moieties, butyl moieties, iso-butyl moieties, and combinations thereof. Typically, $R^b$ is a methyl moiety. For descriptive purposes only, a chemical structure of a $R^b{}_2SiO_{2/2}$ unit is shown below:

$$\begin{array}{c} R^b \\ | \\ -O-Si-O- \\ | \\ R^b \end{array}$$

The aerosol suppressant may include at least one $R^b{}_2SiO_{2/2}$ unit bonded to each of the more than one $SiO_{4/2}$ units. Alternatively, the aerosol suppressant has four blocks of $(CH_3)_2SiO_{2/2}$ units bonded to each of the more than one $SiO_{4/2}$ units. The blocks of the $(CH_3)_2SiO_{2/2}$ units may include from 20 to 400 individual $(CH_3)_2SiO_{2/2}$ units, but are not limited to this range. In one embodiment, the aerosol suppressant has a block from 120 to 500 $(CH_3)_2SiO_{2/2}$ units bonded to each of the more than one $SiO_{4/2}$ units. Typically, the aerosol suppressant has four $SiO_{4/2}$ units and a block from 120 to 500 $(CH_3)_2SiO_{2/2}$ units bonded to each of the four $SiO_{4/2}$ units such that the aerosol suppressant has a total from 1,000 to 5,000 $(CH_3)_2SiO_{2/2}$ units. For descriptive purposes only, a chemical structure of chains of $(CH_3)_2SiO_{2/2}$ units bonded to a $SiO_{4/2}$ unit are shown below wherein n is a number from 20 to 400:

$$\begin{array}{c}
\text{structure showing } R^b{}_2SiO_{2/2} \text{ chains bonded to central } SiO_{4/2} \text{ unit, with } n \text{ repeating units}
\end{array}$$

The aerosol suppressant includes $R^a R^b{}_2 SiO_{1/2}$ units (M units). $R^b$ is the same as $R^b$ described above. $R^a$ is preferably selected from the group of an alkyl moiety having from 1 to 6 carbon atoms, an alkenyl moiety having from 2 to 6 carbon atoms, and an alkynyl moiety having from 2 to 6 carbon atoms. Typically, $R^a$ includes a vinyl moiety. For descriptive purposes only, a chemical structure of a $R^a R^b{}_2 SiO_{1/2}$ unit is shown below:

$$R^a - \underset{\underset{O}{|}}{\overset{\overset{R^b}{|}}{Si}} - R^b$$

Typically, the aerosol suppressant includes a $R^a R^b{}_2 SiO_{1/2}$ unit bonded to each of the at least one $R^b{}_2 SiO_{2/2}$ units thereby capping the aerosol suppressant with functionalized end groups. A chemical structure representative of this arrangement is shown below:

$$-O-\underset{\underset{R^b}{|}}{\overset{\overset{R^b}{|}}{Si}}-O-\underset{\underset{R^b}{|}}{\overset{\overset{R^a}{|}}{Si}}-R^b$$

The aerosol suppressant typically has four $SiO_{4/2}$ units and from 120 to 500 $(CH_3)_2SiO_{2/2}$ units bonded to each of the four $SiO_{4/2}$ units such that the aerosol suppressant has a total from 1,000 to 5,000 $(CH_3)_2SiO_{2/2}$ units. This aerosol suppressant also preferably has eight $R^a R^b{}_2 SiO_{1/2}$ units, i.e., a single $R^a R^b{}_2 SiO_{1/2}$ unit terminally bonded to each of eight terminal $(CH_3)_2SiO_{2/2}$ units, thereby capping the aerosol suppressant with functionalized end groups. For descriptive purposes only, a chemical structure of this particular preferred aerosol suppressant is shown below:

$$\text{[complex branched siloxane structure with vinyl-terminated chains and central } SiO_{4/2} \text{ units]}$$

wherein n is a number from 20 to 400.

The aerosol suppressant has a viscosity from 4,500 to 1,250,000, alternatively from 10,000 to 600,000, and alternatively from 30,000 to 120,000, mPa·s (cP) at 25° C. The viscosity depends, at least in part, on the size and structure of the aerosol suppressant. As such, it is contemplated that the aerosol suppressant is not limited to a particular viscosity. However, in one embodiment, the aerosol suppressant is a gum having a viscosity of greater than 1,250,000 mPa·s (cP) at 25° C.

The aerosol suppressant also preferably has a degree of polymerization from 1,000 to 6,000 and alternatively from 1,000 to 4,000. In one embodiment, the aerosol suppressant has a degree of polymerization of greater than 1,000. In another embodiment, the aerosol suppressant has a degree of polymerization of at least 2,000. In yet another embodiment, the aerosol suppressant has a degree of polymerization of approximately 4,000. The degree of polymerization is a measurement of a number of re-repeating sub-units in a polymer chain.

The aerosol suppressant is present in an amount from 1 to 10, alternatively from 1 to 5, and alternatively from 1 to 4, parts by weight per 100 parts by weight of the composition. However, it is contemplated that the aerosol suppressant may be used in amounts of up to 100 percent by weight of the composition if the aerosol suppressant has a viscosity of less than 4,500, and alternatively of less than 1,000, mPa·s (cP) at 25° C. The aerosol suppressant comprises a polymerization product of a siloxane having units of the chemical formula $(SiO_{4/2})(R^aR^b{}_2SiO_{1/2})_x$ as defined above and a cyclic polysiloxane as described below. The siloxane is preferably polymerized with the cyclic polysiloxane in a weight ratio from 0.2:99.8 to 4:96, alternatively from 0.5:99.5 to 2:98, and alternatively from 0.6:99.4 to 1.2:98.8.

The siloxane contains units of the chemical formula $(SiO_{4/2})(R^aR^b{}_2SiO_{1/2})_x$, wherein $R^a$ and $R^b$ are as described above and x is a number from 1.05 to 4, and alternatively from 1.2 to 4. For descriptive purposes only, the siloxane preferably has the following chemical structure shown below including two $(SiO_{4/2})(R^aR^b{}_2SiO_{1/2})_x$ units wherein x is 2:

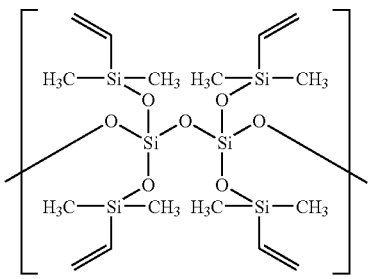

The siloxane has a weight average molecular weight from 246 to 2,000 g/mol. The siloxane also preferably has a viscosity from 20 to 50 mPa·s (cP) at 25° C.

The siloxane may be formed, for example, by reacting approximately 1 mole of $(C_2H_5O)_4Si$ with approximately 1 mole of $((CH_2CH)(CH_3)_2Si)_2O$ and approximately 0.0005 moles of trifluoromethane sulfonic acid. A stoichiometric excess of water may also be used in forming the siloxane. The formation of the siloxane is not limited to the aforementioned reagents and may be formed by any suitable reaction and with any suitable reagents known in the art, such as by methods set forth in U.S. Pat. No. 6,147,243, which is incorporated herein by reference.

The cyclic polysiloxane used in producing the aerosol suppressant typically includes di-functional siloxy units. In one embodiment, the cyclic polysiloxane di-functional siloxy units include at least one alkyl moiety. Suitable non-limiting examples of alkyl moieties include methyl, ethyl, propyl, iso-propyl, butyl, and iso-butyl. Typically, the cyclic polysiloxane is di-functional and includes methyl moieties. The cyclic polysiloxane may include from 3 to 10 $R^a{}_2SiO_{2/2}$ units (D units) wherein $R^a$ is the same as described above. The cyclic polysiloxane may be a dialkylsiloxane ring having from 3 to 6 repeating $R^a{}_2SiO_{2/2}$ units in which each $R^a$ is a methyl. The cyclic polysiloxane is selected from the group of cyclotrisiloxanes, cyclotetrasiloxanes such as octamethylcyclotetrasiloxane, cyclopentasiloxanes such as decamethylcyclopentasiloxane, cyclohexasiloxanes, and combinations thereof. For descriptive purposes only, chemical structures of decamethylcyclopentasiloxane and octamethylcyclotetrasiloxane are shown below:

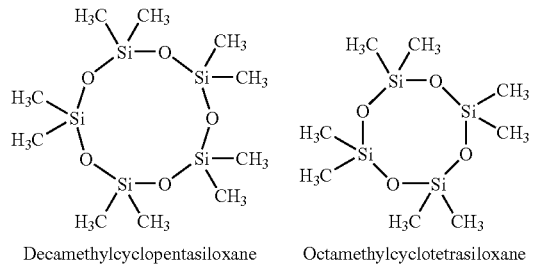

Decamethylcyclopentasiloxane    Octamethylcyclotetrasiloxane

The cyclic polysiloxane typically has a molecular weight from 100 to 750, alternatively from 150 to 500, and alternatively from 275 to 375, g/mol. Cyclic polysiloxanes are commercially available from Dow Corning Corporation of Midland, Mich., under the trade names of Dow Corning® 244 Fluid and Dow Corning® 245 Fluid.

To form the aerosol suppressant, the siloxane and the cyclic polysiloxane are polymerized in the presence of a polymerization catalyst. The type of reaction which forms the aerosol suppressant is either an acid catalyzed or a base catalyzed reaction, dependent on the particular catalyst selected. As such, the polymerization catalyst may be selected from the group of strong acid catalysts, strong base catalysts, and combinations thereof. The strong acid catalyst may be trifluoromethane sulfonic acid and the like. The polymerization catalyst is typically a strong base catalyst. Typically, this strong base catalyst is a phosphazene base catalyst. The phosphazene base catalyst may be any known in the art but typically has the following chemical formula:

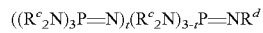

wherein each of $R^c$ and $R^d$ are independently selected from the group of a hydrogen atom, a hydrocarbon, and combinations thereof and t is a number of 1 to 3. If $R^c$ is a hydrocarbon, the hydrocarbon has 1 to 4 carbon atoms. Each $R^c$ may be the same or different in each position and the two $R^c$ groups may be bonded to the same nitrogen (N) atom and linked to complete a heterocyclic ring preferably having 5 or 6 members. If $R^d$ is a hydrocarbon, the hydrocarbon has 1 to 20 carbon atoms, alternatively 1 to 10 carbon atoms.

Alternatively, the phosphazene base catalyst may be a salt and have one of the following alternative chemical formulas:

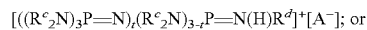

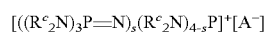

wherein $R^c$, $R^d$, and t are the same as described above and s is a number of 1 to 4. A is an anion and is selected from the group of fluoride, hydroxide, silanolate, alkoxide, carbonate and bicarbonate. In one embodiment, the phosphazene base is an aminophosphazenium hydroxide. The siloxane and the cyclic polysiloxane are polymerized in the presence of 0.1 to 100, alternatively 1 to 50, and alternatively 5 to 20, parts by weight of the phosphazene base catalyst per one million parts by weight of the composition.

In addition to the aerosol suppressant, the composition also includes a curable polysiloxane, which may be any known in the art. Typically, the curable polysiloxane has a degree of polymerization of 50 to 500, alternatively from 100 to 300, and alternatively of about 160. The curable polysiloxane may include a branched siloxane including one or more $SiO_{4/2}$ units, at least 15 $R^a{}_2SiO_{2/2}$ units, and at least one $R^aR^b{}_2SiO_{1/2}$ unit. Curable polysiloxanes can be those disclosed in U.S. Pat. No. 6,806,339, which is incorporated herein by reference. Additional examples of the curable polysiloxanes are disclosed in U.S. Pat. No. 4,609,574 as polydiorganosiloxanes and in WO 03/093369 as organosilicon polymers, both herein incorporated by reference.

The curable polysiloxane may further include a cross-linking agent, a catalyst different from the phosphazene base catalyst, an inhibitor, a release force modifier, and combinations thereof. The cross-linking agent may be an organohydrogenpolysiloxane cross-linking agent present in an amount such that a ratio of a total number of Si—H moieties in the curable polysiloxane to a number of aliphatically unsaturated hydrocarbon moieties in the curable polysiloxane is approximately from 0.9:1 to 3:1, alternatively from 1.1:1 to 2.5:1, and alternatively from 1.2:1 to 2:1. Typically, the cross-linking agent includes at least three Si—H moieties and may have the general chemical formula:

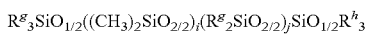

where each $R^g$ may be selected from the group of an alkyl moiety having 1 to 4 carbon atoms and a hydrogen atom, i is a number of zero or greater, and j is a number such that i+j is from 8 to 100.

The catalyst in the curable polysiloxane may include complexes or compounds of group VIII metals, for example, platinum, ruthenium, rhodium, palladium, osmium and iridium. Typical catalysts include platinum compounds and complexes including chloroplatinic acid, platinum acetylacetonate, complexes of platinous halides with unsaturated compounds, for example, ethylene, propylene, organovinylsiloxanes and styrene, hexamethyldiplatinum, $PtCl_2$, $PtCl_3$, and $Pt(CN)_3$. Alternatively the catalyst may be a rhodium complex such as $RhCl_3(Bu_2S)_3$.

The inhibitor in the curable polysiloxane may include ethylenically and/or aromatically unsaturated amides, acetylenic compounds, ethylenically unsaturated isocyanates, olefinic siloxanes, unsaturated hydrocarbon diesters, conjugated eneynes, hydroperoxides, nitrites and diaziridines. methyl butynol, dimethyl hexynol aethynyl cyclohexanol, trimethyl (3,5-dimethyl-1-hexyn-3-oxy)silane, maleates such as Bis(2-methoxy-1-methylethyl)maleate, fumarates such as diethyl-fumarate, fumarate/alcohol mixtures including benzyl alcohol, 1-octanol, and/or ethenyl cyclohexyl-1-ol, and combinations thereof. As is known in the art, inhibitors are utilized to prevent and/or slow a cure of the composition from occurring below a predetermined temperature. It is to be understood that an inhibitor is not required in the composition and that in the absence of the inhibitor, the composition may cure at ambient temperatures.

The release force modifier in the curable polysiloxane may include an alkenylated silicone, an alkenylated polydiorganosiloxane, one or more primary alkenes having from 14 to 30 carbon atoms, and/or one or more branched alkenes having at least 10 carbon atoms. The alkenylated silicone may include at least one alkenylated MQ resin wherein the M units and the Q units may be present in any appropriate ratio. The M units may include trialkyl siloxy and/or dialkyl alkenyl siloxy moieties. The alkenyl moiety may be a cyclohexenyl, vinyl, propenyl, butenyl, pentenyl and/or a hexenyl moiety. Typically, the alkenyl moiety is a vinyl or hexenyl moiety. The alkyl moieties may be any suitable alkyl moieties, but are most preferably methyl moieties. The alkenylated polydiorganosiloxane typically includes an alkenyldialkyl silyl terminated polydiorganosiloxane including D units including an alkyl moiety having from 1 to 6 carbon atoms and/or an alkenyl moiety such as a vinyl or hexenyl moiety. The one or more primary alkenes may include any primary alkene having from 10 to 30 carbon atoms such as tetradecene and octadecene.

Branched alkenes, as the release force modifier, may have the following chemical formula:

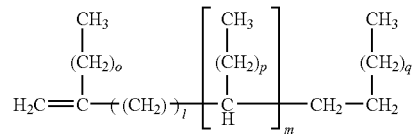

wherein 1 is number of methylene moieties and m is the number of branched alkyl moieties such that each of 1 and m are numbers from 0 to 20 and each of 1 and m is randomly distributed. Additionally, o, p, and q may be numbers from 1 to 12. Typically, the total number of carbon atoms in each branched alkene is at least 20. Typically, the curable polysiloxane includes from 15 to 75 parts by weight of the release force modifier per 100 parts by weight of the curable polysiloxane.

The composition may further include dialkyl alkenyl silyl terminated polydiorganosiloxanes, reactive diluents, adhesion promoters, solvents, fragrances, preservatives, bath life extenders, and fillers such as silica, quartz and chalk. Suitable examples of bath life extenders include primary or secondary alcohols, aliphatic and aromatic alcohols with fewer than 10 carbon atoms such as methanol, ethanol, propanol phenol and cyclohexanol, carboxylic acids, cyclic ethers, and combinations thereof.

The present invention also provides a method of forming the composition. The method comprises combining the aerosol suppressant and the curable polysiloxane to form the composition.

While the composition may be formed by merely combining the aerosol suppressant and the curable polysiloxane, in addition to any optional components, it may be more desirable to prepare the composition in separate parts or packages i.e. in the form of a kit. In such a case the aerosol suppressant, the curable polysiloxane, and any optional components are combined at the time the composition is to be applied to a substrate. It is contemplated that the kit may include a first part including the aerosol suppressant and a second part including the curable polysiloxane with any or all of the optional components included in either the first and/or second parts.

The present invention further provides a method of coating the substrate in a release coating process. The method of coating the substrate comprises forming the composition and thereafter applying the composition to the substrate. Examples of suitable substrates include paper, metal, plastic, cardboard, fabrics, films, and combinations thereof. The films may include polyethylene, polypropylene, polyester, polystyrene, oriented polypropylene, biaxially oriented polypropylene, and combinations thereof.

The composition is typically applied to the substrate at rates of speed in excess of 305 m/min, but may be applied at slower speeds, if desired by one of skill in the art. The composition may be applied solventless, in a solvent, or as part of an oil-in-water emulsion. Typically, the composition is substantially free of solvents. The terminology "substantially free" includes an amount of solvents in the process that is less than 0.5% by weight of the composition.

The composition produces a mist of less than 50, alternatively of less than 20, alternatively of less than 15, and alternatively of less than 5, mg/m$^3$ measured at about 457 meters per minute as determined using a laboratory 2-roll coater manufactured by Euclid Tool and Machines of Bay City, Mich. and an attached Model 8520 DustTrak® Aerosol Monitor instrument, manufactured by TSI Corporation, St. Paul, Minn. Since the measurement of mist is sensitive to environmental variables, the entire apparatus for measuring mist is disposed in a laboratory hood to minimize any influence of air turbulence on the measurement of misting. A vacuum cleaner is attached to each roll surface to sweep the mist away once it has passed a measuring point. To obtain consistent results, pressure settings of the top blade and the top roller are preferably kept at about 70,000 Pa and about 345,000 Pa, respectively, and the bottom blade is preferably used as a doctoring blade to regulate the amount of the composition exposed to the top and bottom rolls.

After the mist is produced, the air borne particles of the composition are drawn to the DustTrak® Aerosol Monitor and analyzed. The DustTrak® Monitor is capable of measuring the total number of aerosol particles in a sample of air drawn through at approximately 3 liters per minute for a set sample time. In the following examples, the mist is determined by measurement for a thirty second sample time.

EXAMPLES

A series of Aerosol Suppressants (Suppressants 1-6) were formed. For each of the Suppressants 1-6, the Siloxane, the Cyclic Polysiloxane, and the Diluent were combined in a reaction vessel at 25° C. and formed a mixture. Then, the Phosphazene Base Catalyst was added to the mixture which was thoroughly mixed at 25° C. The resulting mixture was then brought to a desired reaction temperature of approximately 140° C.-150° C. and mixed at that temperature for a time sufficient for the viscosity of the forming Suppressants 1-6 to stabilize. Subsequently, an optional Complexing Agent was added upon completion of the reaction to inhibit the activity of the Phosphazene Base Catalyst and stabilize the Suppressants 1-6. The chemical identities and amounts of each of the reactants are set forth in Table 1 wherein all amounts are in parts by weight. Additionally, each of the Suppressants 1-6 and the Siloxane itself were evaluated to determine % Vinyl Concentration, Viscosity (cs), Weight Average Molecular Weight, Polydispersity, a Ratio of M to Q units, and a ratio of equivalents of $SiO_{4/2}$ units to dimethylsiloxane units. The results of these evaluations are also set forth in Table 1 below.

TABLE 1

| Components | Suppressant 1 | Suppressant 2 | Suppressant 3 |
|---|---|---|---|
| Siloxane | 2.7 | 2 | 1.6 |
| Cyclic Polysiloxane | 297.3 | 298 | 298.4 |
| Phosphazene Base Catalyst | 0.005 | 0.005 | 0.005 |
| Diluent | 0.06 | 0.06 | 0.06 |
| Complexing Agent | 0.01 | 0.01 | 0.01 |
| % Vinyl Concentration | 0.197 | 0.146 | 0.101 |
| Viscosity (mPa · s) (cP) at 25° C. | 15,240 | 29,760 | 121,600 |
| Weight Average Molecular Weight (g/mol) | — | — | — |
| Polydispersity | — | — | — |
| Ratio of M to Q Units | — | — | — |
| Normalized Ratio of Equivalents of $SiO_{4/2}$ Units to Dimethylsiloxane Units | 1:367 | 1:502 | 1:619 |

| Components | Suppressant 4 | Suppressant 5 | Suppressant 6 | Siloxane |
|---|---|---|---|---|
| Siloxane | 2.7 | 9 | 7.5 | — |
| Cyclic Polysiloxane | 297.3 | 1991 | 1992.5 | — |
| Phosphazene Base Catalyst | 0.005 | 0.02 | 0.02 | — |

TABLE 1-continued

| | | | | |
|---|---|---|---|---|
| Diluent | 0.03 | 0.03 | 0.03 | — |
| Complexing Agent | 0.009 | 0.04 | 0.04 | — |
| % Vinyl Concentration | 0.17 | 0.086 | 0.071 | 19.5 |
| Viscosity (mPa · s) (cP) at 25° C. | 21,600 | 315,200 | 1,230,000 | 120 |
| Weight Average Molecular Weight (g/mol) | 53,100 | 93,400 | 103,000 | — |
| Polydispersity | 9.3 | 10.66 | 11.7 | — |
| Ratio of M to Q Units | — | — | — | 1.91 |
| Normalized Ratio of Equivalents of $SiO_{4/2}$ Units to Dimethylsiloxane Units | 1:367 | 1:751 | 1:967 | — |

The Siloxane was formed by reacting 208.33 grams (1 mole) of $(C_2H_5O)_4Si$ with 186.40 grams (1 mole) of $((CH_2CH)(CH_3)_2Si)_2O$, and 0.08 grams (0.0005 mol) of trifluoromethane sulfonic acid followed by addition of 36.93 grams (2.05 moles) of $H_2O$.

The Cyclic Polysiloxane is decamethylcyclopentasiloxane.

The Phosphazene Base Catalyst is a trimethyl amine hydroxide phosphazene.

The Diluent is potassium silanolate and has an equivalent weight per potassium of 10,000.

The Complexing Agent is trimethyl silyl phosphate and is commercially available from Gelest, Inc. of Morrisville, Pa. under the trade name of tris(trimethylsilyl)phosphate.

The % Vinyl Concentration represents a percentage of vinyl groups in the Suppressants 1-6 or the Siloxane on a weight basis and was calculated using an iodine titration method well known in the art.

The Viscosity of the Suppressants 1-6 and the Siloxane was measured using a Brookfield Viscometer using an LV 4 Spindle at room temperature.

The Weight Average Molecular Weight of the Suppressants 1-6 and the Siloxane was determined using a gel permeation chromatography method well known in the art.

The Polydispersity of the Suppressants 1-6 and the Siloxane was determined using a gel permeation chromatography method well known in the art.

The Ratio of M to Q Units in the Suppressants 1-6 and the Siloxane was determined using a $^{29}Si$ NMR method well known in the art.

Additionally, two comparative aerosol suppressants, Comparative Suppressants 1 and 2, were also formed. The Comparative Suppressants 1 and 2 each included a branched silicone polymer formed by combining a methylhydrogensiloxane (A), an alkenyl siloxane (B), an unsaturated organic compound (C), and a catalyst (D) at 25° C. together to form a mixture. The temperature of the mixture was raised to the reaction temperature and the mixture was mixed at that temperature for a time sufficient to completely hydrosilylate all vinyl groups and for the viscosity to stabilize. Upon completion of the reaction, an inhibitor (E) was added to the mixture to inhibit activity of the catalyst (D) and stabilize the branched silicone polymer. The chemical identities and amounts of each of the aforementioned reactants are set forth in Table 2 wherein all amounts are in parts by weight unless otherwise noted. The reaction conditions, ratio of silane groups (SiH) to vinyl groups, and viscosity of the Comparative Suppressants 1 and 2 are also set forth in Table 2. Each of the Comparative Suppressants 1 and 2 is further described in U.S. Pat. No. 6,805,914.

TABLE 2

| Components | Comparative Suppressant 1 | Comparative Suppressant 2 |
|---|---|---|
| Methylhydrogensiloxane (A) | 59.7 | 59.1 |
| Alkenyl Siloxane (B1) | 21 | — |
| Alkenyl Siloxane (B2) | — | 20.6 |
| Unsaturated Organic Compound (C) | 8.4 | 9.7 |
| Catalyst (D) | 0.05 | 0.05 |
| Inhibitor (E) | 0.1 | 0.1 |
| SiH:Vinyl Ratio | 7.7:1 | 219:1 |
| Reaction Time (hrs) | 1 | 1 |
| Reaction Temperature (° C.) | 80 | 100 |
| Viscosity (mPa·s) (cP) at 25° C. | 750 | 1130 |

Methylhydrogensiloxane (A) is a trimethylsiloxy-terminated polydimethylsiloxane-polymethylhydrogensiloxane copolymer having a total average degree of polymerization of about 10 with about 50 mol % methylhydrogen moiety on a siloxane chain and a viscosity of about 5 mPa·s (cP) at 25° C.

Alkenyl Siloxane (B1) is a dimethylvinylsiloxy-terminated polydimethylsiloxane polymer having an average degree of polymerization of about 5 and a viscosity of about 3 mPa·s (cP) at 25° C.

Alkenyl Siloxane (B2) is a dimethylvinylsiloxy-terminated polydimethylsiloxane polymer having an average degree of polymerization of about 130 and a viscosity of about 300 mPa·s (cP) at 25° C.

Unsaturated Organic Compound (C) is alpha-methylstyrene commercially available from Sigma Aldrich Corporation of St. Louis, Mo.

Catalyst (D) is a soluble platinum complex containing 0.67 wt. % platinum, formed from chloroplatinic acid and divinyltetramethyldisiloxane.

Inhibitor (E) is bis(2-methoxy-1-methylethyl)maleate.

After formation of the Suppressants 1-6 and the Comparative Suppressants 1 and 2, samples of each of the Suppressants 1-6 and the Comparative Suppressants 1 and 2 were combined with a Curable Polysiloxane to form samples of the composition (Compositions 1-9) and samples of the comparative compositions (Comparative Compositions 1 and 2).

The Curable Polysiloxane was formed by combining 21.6 grams of a $(Vinyl(CH_3)_2SiO_{1/2})_4)(SiO_{4/2})$ polysiloxane with 592 grams of octamethylcyclotetrasiloxane and 1.2 grams trifluoromethane sulfonic acid to form a reaction mixture. The reaction mixture was stirred for six hours at a temperature from 80 to 90° C. and then cooled to room temperature. Approximately 1 gram of calcium carbonate was then added and the mixture was stirred for three hours. Finally the mixture was stripped at a temperature of approximately 150° C. and a pressure of 40 millibars, for 2 hours.

The amounts of each of the Suppressants 1-6 and the Comparative Suppressants 1 and 2 present in the Compositions 1-9 and the Comparative Compositions 1 and 2, respectively, are set forth in Table 3 below, wherein all amounts are in weight percent unless otherwise indicated.

TABLE 3

| | Composition 1 | Composition 2 | Composition 3 | Composition 4 |
|---|---|---|---|---|
| Suppressant 1 | 16 | — | — | — |
| Suppressant 2 | — | 16 | — | — |
| Suppressant 3 | — | — | 16 | 8 |
| Suppressant 4 | — | — | — | — |
| Suppressant 5 | — | — | — | — |
| Suppressant 6 | — | — | — | — |
| Comparative Suppressant 1 | — | — | — | — |
| Comparative Suppressant 2 | — | — | — | — |
| Curable Polysiloxane | 384 | 384 | 384 | 392 |

| | Composition 5 | Composition 6 | Composition 7 | Composition 8 |
|---|---|---|---|---|
| Suppressant 1 | — | — | — | — |
| Suppressant 2 | — | — | — | — |
| Suppressant 3 | — | — | 4 | — |
| Suppressant 4 | 4 | — | — | — |
| Suppressant 5 | — | 4 | — | 4 |
| Suppressant 6 | — | — | — | — |
| Comparative Suppressant 1 | — | — | — | — |
| Comparative Suppressant 2 | — | — | — | — |
| Curable Polysiloxane | 396 | 396 | 396 | 396 |

| | Composition 9 | Comparative Composition 1 | Comparative Composition 2 |
|---|---|---|---|
| Suppressant 1 | — | — | — |
| Suppressant 2 | — | — | — |
| Suppressant 3 | — | — | — |
| Suppressant 4 | — | — | — |
| Suppressant 5 | — | — | — |
| Suppressant 6 | 4 | — | — |
| Comparative Suppressant 1 | — | 8 | — |
| Comparative Suppressant 2 | — | — | 8 |
| Curable Polysiloxane | 396 | 392 | 392 |

After formation, samples of each of the Compositions 1-9 and the Comparative Compositions 1 and 2 were applied to the rollers of the 2-roll coater at about 457 meters/min and measured for misting. To determine an amount of misting of each of the Compositions 1-9 and the Comparative Compositions 1 and 2, 10 separate measurements of mist were recorded and averaged. The average measurements, including the standard deviations, for each of the Compositions 1-9 and the Comparative Compositions 1 and 2 are set forth in Table 4 below. Comparative Composition 1 was tested for mist in four separate experiments and the total average and total standard deviation of forty separate measurements of mist are presented below in Table 4.

TABLE 4

| | Composition 1 | Composition 2 | Composition 3 | Composition 4 |
|---|---|---|---|---|
| Average Mist (mg/m³) | 15.5 | 13.9 | 7.7 | 13.5 |
| Standard Deviation | 0.7 | 0.4 | 0.4 | 0.8 |

| | Composition 5 | Composition 6 | Composition 7 | Composition 8 |
|---|---|---|---|---|
| Average Mist (mg/m³) | 12.9 | 14.1 | 16 | 18.2 |
| Standard Deviation | 0.4 | 0.6 | 0.6 | 0.9 |

TABLE 4-continued

|  | Composition 9 | Comparative Composition 1 | Comparative Composition 2 |
|---|---|---|---|
| Average Mist (mg/m$^3$) | 13.6 | 21.4 | >150* |
| Standard Deviation | 0.7 | 2 | N/A |

*Single measurement that exceeds measurement capabilities of DustTrak ® Monitor

The results of the measurement of the Average Mist demonstrate that the Compositions 1-9 of the instant invention are able to be applied to substrates with reduced misting as compared to the Comparative Compositions 1 and 2. This reduction is mist reduces production nuisances and reduces waste of the composition, thereby decreasing production costs.

Obviously, many modifications and variations of the present invention are possible in light of the above teachings. The invention may be practiced otherwise than as specifically described within the scope of the appended claims.

What is claimed is:

1. A release coating composition comprising:
  A. an aerosol suppressant having more than one SiO$_{4/2}$ unit and comprising a polymerization product of;
    (1) a siloxane containing units of the chemical formula (SiO$_{4/2}$)(R$^a$R$^b_2$SiO$_{1/2}$)$_x$
    wherein R$^a$ is selected from the group of an alkyl moiety having from 1 to 6 carbon atoms, an alkenyl moiety having from 2 to 6 carbon atoms, and an alkynyl moiety having from 2 to 6 carbon atoms, R$^b$ is selected from the group of an alkyl moiety having from 1 to 6 carbon atoms, an aryl moiety, an alkoxy moiety, an acrylate moiety, and a methacrylate moiety, and x is a number from 1.05 to 2, and
    (2) a cyclic polysiloxane,
    wherein said siloxane and said cyclic polysiloxane are polymerized in the presence of a polymerization catalyst; and
    wherein said aerosol suppressant has a viscosity of from 30,000 to 1,250,000 mPa·s at 25° C.; and
  B. a curable polysiloxane.

2. A composition as set forth in claim 1 wherein said polymerization catalyst is selected from the group of strong acid catalysts, strong base catalysts, and combinations thereof.

3. A composition as set forth in claim 2 wherein said strong acid catalyst is further defined as trifluoromethane sulfonic acid.

4. A composition as set forth in claim 2 wherein said strong base catalyst is further defined as a phosphazene base catalyst.

5. A composition as set forth in claim 1 wherein said aerosol suppressant has more than one and less than 4 SiO$_{4/2}$ units.

6. A composition as set forth in claim 5 wherein said aerosol suppressant has from 2 to less than 4 SiO$_{4/2}$ units.

7. A composition as set forth in claim 1 wherein said aerosol suppressant further contains at least one R$^b_2$SiO$_{2/2}$ unit bonded to each of said more than one SiO$_{4/2}$ units.

8. A composition as set forth in claim 7 wherein said aerosol suppressant has four blocks of (CH$_3$)$_2$SiO$_{2/2}$ units bonded to each of said more than one SiO$_{4/2}$ units.

9. A composition as set forth in claim 7 wherein said aerosol suppressant has from 1,000 to 5,000 (CH$_3$)$_2$SiO$_{2/2}$ units.

10. A composition as set forth in claim 1 wherein said aerosol suppressant has eight R$^a$R$^b_2$SiO$_{1/2}$ units.

11. A composition as set forth in claim 1 wherein said aerosol suppressant has a degree of polymerization from 1,000 to 4,000.

12. A composition as set forth in claim 1 wherein said aerosol suppressant is present in an amount from 1 to 5 parts by weight per 100 parts by weight of said composition.

13. A composition as set forth in claim 1 wherein said siloxane is polymerized with said cyclic polysiloxane in a weight ratio from 0.2:99.8 to 4:96.

14. A composition as set forth in claim 1 producing a mist of less than 50 mg/cubic meter when applied to a substrate at about 457 meters per minute.

15. A composition as set forth in claim 1 wherein said aerosol suppressant has four SiO$_{4/2}$ units, from 360 to 1,600 (CH$_3$)$_2$SiO$_{2/2}$ units bonded to each of said four SiO$_{4/2}$ units, eight (CH$_3$)$_2$(CH$_2$CH)SiO$_{1/2}$ units terminally bonded to four of said (CH$_3$)$_2$SiO$_{2/2}$ units, and is present in an amount from 1 to 5 parts by weight per 100 parts by weight of said composition, and wherein R$^a$ is a vinyl moiety, R$^b$ is a methyl moiety, said siloxane is polymerized with said cyclic polysiloxane in a weight ratio from 0.2:99.8 to 4:96, said cyclic polysiloxane is selected from the group of decamethylcyclopentasiloxane, octamethylcyclotetrasiloxane, and combinations thereof, said polymerization catalyst is a phosphazene base catalyst of the chemical formula:

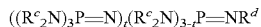

wherein each of R$^c$ and R$^d$ are independently selected from the group of a hydrogen atom, a hydrocarbon, and combinations thereof and t is a number from 1 to 3, and said composition produces a mist of less than 50 mg/cubic meter when applied to a substrate at about 457 meters per minute.

16. A composition as set forth in claim 1 wherein said aerosol suppressant has a viscosity of from 30,000 to 120,000 mPa·s at 25° C.

17. A composition as set forth in claim 1 wherein said aerosol suppressant has a viscosity of from 30,000 to 600,000 mPa·s at 25° C.

18. A composition as set forth in claim 1 wherein said aerosol suppressant has two SiO$_{4/2}$ units.

19. A composition as set forth in claim 1 wherein x is 2.

20. A method of forming a release coating composition, said method comprising the steps of:
  A. polymerizing a siloxane having units of the chemical formula (SiO$_{4/2}$)(R$^a$R$^b_2$SiO$_{1/2}$)$_x$ wherein R$^a$ is selected from the group of an alkyl moiety having from 1 to 6 carbon atoms, an alkenyl moiety having from 2 to 6 carbon atoms, and an alkynyl moiety having from 2 to 6 carbon atoms, R$^b$ is selected from the group of an alkyl moiety having from 1 to 6 carbon atoms, an aryl moiety, an alkoxy moiety, an acrylate moiety, and a methacrylate moiety, and x is a number from 1.05 to 2, with a cyclic polysiloxane in the presence of a polymerization catalyst to form an aerosol suppressant having more than one SiO$_{4/2}$ unit and having a viscosity of from 30,000 to 1,250,000 mPa·s at 25° C.; and
  B. combining the aerosol suppressant and a curable polysiloxane to form the release coating composition.

21. A method as set forth in claim 20 wherein the polymerization catalyst is selected from the group of strong acid catalysts, strong base catalysts, and combinations thereof.

22. A method as set forth in claim 20 wherein the polymerization catalyst is further defined as a phosphazene base catalyst.

23. A method as set forth in claim 20 wherein the aerosol suppressant has more than one and less than 4 $SiO_{4/2}$ units.

24. A method as set forth in claim 20 wherein the composition produces a mist of less than 50 mg/cubic meter when applied to a substrate at about 457 meters per minute.

25. A method of coating a substrate in a release coating process, said method comprising the steps of:
  A. polymerizing a siloxane having units of the chemical formula $(SiO_{4/2})(R^a R^b{}_2 SiO_{1/2})_x$ wherein $R^a$ is selected from the group of an alkyl moiety having from 1 to 6 carbon atoms, an alkenyl moiety having from 2 to 6 carbon atoms, and an alkynyl moiety having from 2 to 6 carbon atoms, $R^b$ is selected from the group of an alkyl moiety having from 1 to 6 carbon atoms, an aryl moiety, an alkoxy moiety, an acrylate moiety, and a methacrylate moiety, and x is a number from 1.05 to 2, with a cyclic polysiloxane in the presence of a polymerization catalyst to form an aerosol suppressant having more than one $SiO_{4/2}$ unit and having a viscosity of from 30,000 to 1,250,000 mPa·s at 25° C.; and
  B. combining the aerosol suppressant and a curable polysiloxane to form a release coating composition; and
  C. applying the release coating composition to the substrate in the release coating process.

26. A method as set forth in claim 25 wherein the polymerization catalyst is selected from the group of strong acid catalysts, strong base catalysts, and combinations thereof.

27. A method as set forth in claim 25 wherein the polymerization catalyst is further defined as a phosphazene base catalyst.

28. A method as set forth in claim 25 wherein the aerosol suppressant has more than one and less than 4 $SiO_{4/2}$ units.

29. A method as set forth in claim 25 producing a mist of less than 50 mg/cubic meter when the composition is applied to the substrate at about 457 meters per minute.

* * * * *